(12) United States Patent
Reddy et al.

(10) Patent No.: US 9,661,855 B2
(45) Date of Patent: May 30, 2017

(54) CYCLIC AZA-SILA COMPOUNDS AS INSECT REPELLANTS

(71) Applicant: COUNCIL OF SCIENTIFIC & INDUSTRIAL RESEARCH, New Delhi (IN)

(72) Inventors: Dumbala Srinivasa Reddy, Pune (IN); Remya Ramesh, Pune (IN); Seetharam Singh Balamkundu, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/654,383

(22) PCT Filed: Dec. 23, 2013

(86) PCT No.: PCT/IN2013/000791
§ 371 (c)(1),
(2) Date: Jun. 19, 2015

(87) PCT Pub. No.: WO2014/097322
PCT Pub. Date: Jun. 26, 2014

(65) Prior Publication Data
US 2015/0342191 A1    Dec. 3, 2015

(30) Foreign Application Priority Data
Dec. 21, 2012    (IN) ............................ 3958/DEL/2012

(51) Int. Cl.
*C07F 7/08*    (2006.01)
*A01N 55/00*    (2006.01)

(52) U.S. Cl.
CPC ............ *A01N 55/00* (2013.01); *C07F 7/0816* (2013.01); *C07F 7/0832* (2013.01)

(58) Field of Classification Search
CPC .................................. A01N 55/00; C07F 7/08
USPC ........................................................ 556/406
See application file for complete search history.

(56) References Cited

PUBLICATIONS

Buswell et al., Org. Biomol. Chem., 2004, 2 3006-3017.*
Bhattacharjee, A.K. et al.: "Predicting Mosquito Repellent Potency of N,N-Diethyl-m-Toluamide (DEET) Analogs From Molecular Electronic Properties", Am. J. Trop. Med. Hyg., vol. 60, (1999), pp. 1-6.
Buswell, M. et al: "The Extraordinary Reactions of Phenyldimethylsilyllithium with N,N-disubstituted Amides", Org. Biomol. Chem., vol. 2, (2004), pp. 3006-3017.
Database CA [Online]—Chemical Abstracts Service, Columbus, Ohio, US; Buswell, Marina: "Reactions of the Dimethylphenlysilylithium Reagent with Tertiary Amides", XP002721751, retrieved from STN Database accession No. 2012:1448519.
Garner, D.D. et al.: "Silyl Ether Precursor-Type Insect Repellents", Journal of Medicinal Chemistry, vol. 16, No. 6, (1973), pp. 729-732.
International Search Report for PCT/IN2013/000791 dated Apr. 1, 2014.
Lukevics, E.: "Biological Activity of Nitrogen-Containing Organosilicon Compounds", Nobel Foundation Symposia, Biochemistry of Silicon and Related Problems, vol. 40, (1978), pp. 435-445.
Lukevits, E.: "Nitrogen-containing organisilicon compounds XLIX. Sysnthesis and insect repellent properties of Si-substituted (amenomethyl) silanes (CH3)n(RO)3-nSiCH2NR'R", Pharmaceutical Chemistry Journal, vol. 8, Issue 10, (Oct. 1974), pp. 611-613.

* cited by examiner

*Primary Examiner* — Sudhakar Katakam
*Assistant Examiner* — Kofi Adzamli
(74) *Attorney, Agent, or Firm* — Norton Rose Fulbright US LLP

(57) ABSTRACT

The invention relates to aza-sila compounds of Formula (I), useful as insect repellants. wherein, 'A' is selected from the group consisting of branched or unbranched (C I-CI 2) alkyl, branched or unbranched (CI-CI 2) alkynyl; and substituted or unsubstituted 4 to 6 membered acyclic saturated or unsaturated compounds, wherein the substituents are selected from the group consisting of halogen, hydrogen, (CI-C6) alkyl, aryl, arylalkyl and heterocyclic; or 'A' is independently selected from the group consisting of the following moiety: Formula (II) wherein, X and Y are identical or different and independently selected from the group consisting of —C—, —N, —O, and —S; where R1, R2, R3, and R4 are identical or different and are independently selected from the group consisting of hydrogen, halogen, linear or branched (C1-C6) alkyl, aryl, arylalkyl, hydroxyl, and heterocyclic; and wherein, the halogen is selected from the group consisting of —Cl, —I, —Br, and —F. The invention further discloses a process for the preparation of the compounds of Formula (I).

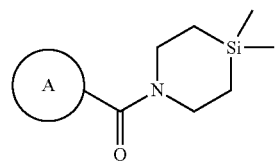

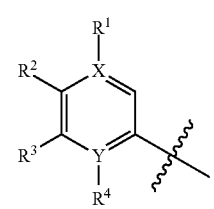

7 Claims, No Drawings

CYCLIC AZA-SILA COMPOUNDS AS INSECT REPELLANTS

CROSS-REFERENCE TO RELATED APPLICATIONS

This application is a national phase application under 35 U.S.C. §371 of International Application No. PCT/IN2013/000791 filed 23 Dec. 2013, which claims priority to Indian Patent Application No. 3958/DEL/2012 filed 21 Dec. 2012. The entire contents of each of the above-referenced disclosures is specifically incorporated herein by reference without disclaimer.

FIELD OF THE INVENTION

The present invention relates to cyclic aza-sila compounds of Formula I, useful as insect repellents. The invention further relates to the process for preparation of the compounds of Formula I.

BACKGROUND OF THE INVENTION

Vector-borne diseases are still a major mortality factor in Africa and South-east Asia and effective mosquito repellents are therefore needed. DEET, chemically known as N,N-Diethyl-meta-toluamide, of DEET, is a slightly yellow oil, which is commonly used active ingredient in insect repellents to prevent bites from insects such as mosquitoes, biting flies, fleas and small flying insects.

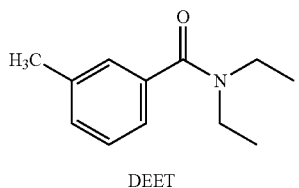

DEET

DEET was first developed by the United States Army during World War II as early as 1946. DEET is applied to the skin or to clothing in different dosage forms to provide protection against tick bites, mosquito bites, and other insects that can transmit diseases.

DEET is regularly sold and used as spray or lotion in concentrations up to 100%. Consumer Reports found a direct correlation between DEET concentration and hours of protection that gives against insect bites. It was found that a 100% DEET offers up to 12 hours of protection while lower concentrations of 20%-40% offers 3 to 8 hours of protection. The Center for Disease Control recommends 30-50% concentration of DEET to prevent the spread of pathogens carried by insects.

N,N-Diethyl-m-toluamide (DEET) is one of the most effective and commonly used mosquito repellents. However, there are recent reports about the insect resistance to DEET, particularly, mosquitoes. Therefore, the search for new insect repellents is an important area of research to fight against the threat posed by increased number of infections indirectly caused by various insects. The synthesis of novel insect repellents is in demand, as insects are developing resistance to commonly used insect repellents such as DEET. Since, DEET is not reported to have any adverse health issues in animal; the research is progressing in search of novel analogs of DEET which are more or equally effective as DEET while addressing the issue of DEET resistance. There are few reports on novel analogs of DEET as insect repellents. One such report in an article titled "Biting deterrent activity of a DEET analog, two DEPA analogs, and SS220 applied topically to human volunteers compared with DEET against three species of blood-feeding flies" published in J Med, Entomol. 2006 November; 43(6): 1248-51, discloses that two DEPA analogs, N,N-diethyl(3-bromophenyl) acetamide and N,N-diethyl[(alpha,alpha,alpha-trifluoro-m-tolyl)]acetamide, and one DEET analog, N,N,diethyl[3-(trifluoromethyl)]benzamide, had biting-deterrent activities that were superior to DEET against *Aedesaegypti* (L.) and *Anopheles stephensi* Liston.

Further insect repellent activity of Si-substituted amino methyl silane is reported in *Pharmaceutical Chemistry Journal* October 1974, volume 8, issue 10, pp 611-613 by É. Lukevits et al. Article titled "Biological Activity of Nitrogen-Containing Organosilicon Compounds" by E. Lukevics in *Nobel Foundation Symposia* Volume 40, 1978, pp 435-445 discloses organosilicon derivatives of amino-alcohols having insect-repellent and anti-microbial properties. Bhattacharjee A K et al. in *Am J Trop Med Hyg*. 1999 January; 60 (1): 1-6 discloses specific molecular electronic properties of N,N-diethyl-m-toluamide (DEET) analogs and their insect repellent efficacy.

In view of the foregoing, there is definite need in the art to provide effective insect repellants to address the public health issues.

OBJECTS OF THE INVENTION

The main object of the present invention is to provide cyclic aza-sila compounds of Formula I useful as insect repellents. Another object of the present invention is to provide a process for the preparation of cyclic aza-sila compounds.

SUMMARY OF THE INVENTION

Accordingly, the present invention provides cyclic aza-sila compounds of Formula I:

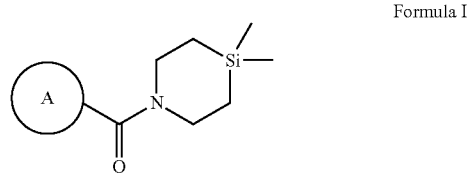

Formula I wherein, 'A' is selected from the group consisting of branched or unbranched (C1-C12) alkyl, branched or unbranched (C1-C12) alkynyl; and substituted or unsubstituted 4 to 6 membered acyclic or cyclic saturated or unsaturated compounds, wherein the substituents are selected from the group consisting of halogen, hydrogen, (C1-C6) alkyl, aryl, arylalkyl, and heterocyclic;

or 'A' is independently selected from the group consisting of the following moiety:

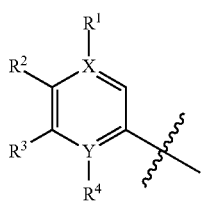

wherein, X and Y are identical or different and independently selected from the group consisting of C—, —N, —O, and —S;

where R1, R2, R3, and R4 are identical or different and are independently selected from the group consisting of hydrogen, halogen, linear or branched (C1-C6) alkyl, aryl, arylalkyl, hydroxyl, and heterocyclic; and wherein, the halogen is selected from the group consisting of —Cl, —I, —Br and —F.

In an embodiment of the present invention, the representative compounds of Formula I are selected from the group consisting of:
(4,4-Dimethyl-1,4-azasilinan-1-yl)(phenyl)methanone [compound 4];
(2,5-dichlorophenyl)(4,4-dimethyl-1,4-azasilinan-1-yl) methanone [compound 6];
Cyclohex-1-en-1-yl(4,4-dimethyl-1,4-azasilinan-1-yl) methanone [compound 7];
Cyclopent-1-en-1-yl(4,4-dimethyl-1,4-azasilinan-1-yl) methanone [compound 8];
(4,4-Dimethyl-1,4-azasilinan-1-yl)(pyridin-2-yl)methanone [compound 9];
(4,4-Dimethyl-1,4-azasilinan-1-yl)(pyrazin-2-yl)methanone [compound 10];
(2-Chlorophenyl)(4,4-dimethyl-1,4-azasilinan-1-yl)methanone [compound 11];
(4,4-Dimethyl-1,4-azasilinan-1-yl)(m-tolyl)methanone [compound 12];
1-(4,4-Dimethyl-1,4-azasilinan-1-yl)undec-10-en-1-one [compound 13];
Cyclobutyl(4,4-dimethyl-1,4-azasilinan-1-yl)methanone [compound 14];
1-(4,4-Dimethyl-1,4-azasilinan-1-yl)-3-methylbut-2-en-1-one [compound 15];
(4,4-Dimethyl-1,4-azasilinan-1-yl)(o-tolyl)methanone [compound 16];
(4,4-Dimethyl-1,4-azasilinan-1-yl)(p-tolyl)methanone [compound 17];
Cyclohex-3-en-1-yl(4,4-dimethyl-1,4-azasilinan-1-yl) methanone [compound 18];
Cyclopentyl-(4,4-dimethyl-1,4-azasilinan-1-yl)methanone [compound 19];
1-(4,4-Dimethyl-1,4-azasilinan-1-yl)undecan-1-one [compound 20];
1-(4,4-Dimethyl-1,4-azasilinan-1-yl)hexan-1-one [compound 22];
1-(4,4-Dimethyl-1,4-azasilinan-1-yl)-3-methylbutan-1-one [compound 23]; and
Cyclohexyl(4,4-dimethyl-1,4-azasilinan-1-yl)methanone [compound 24].

In still another embodiment of the present invention, the cyclic aza-sila compound of Formula I are useful as insect repellents.

In yet another embodiment of the present invention, a process for preparation of cyclic aza-sila compounds of Formula I, wherein the process comprises the steps of:

(a) acid-amine coupling of 4,4-dimethyl-1,4-azasilinane 3 with a substituted carboxylic acid in presence of EDC.HCl(1-Ethyl-3-(3-dimethylaminopropyl)carbodiimide hydrochloride) and HOBt (Hydroxybenzotriazole) as coupling reagents in an organic base to obtain compounds selected from the group consisting of compound 6, compound 7, compound 8, compound 9, compound 10, compound 11, compound 12, compound 13, compound 14, compound 15, compound 16, compound 17, and compound 18;

(b) optionally hydrogenating a compound selected from the group consisting of compound 8, 13, 15, and 18, as obtained in step (a) or compound 21 in ethanol by adding 10% Pd on carbon followed by stirring at room temperature for 1 h under Hydrogen atmosphere to obtain a compound selected from the group consisting of compound 19, 20, 23, 24, and 22 respectively.

In still another embodiment of the present invention, the carboxylic acid used in step (a) of a process for preparation of cyclic aza-sila compounds of Formula I, is selected from the group consisting of cyclohexene carboxylic acid, cyclopentene carboxylic acid, pyridine carboxylic acid, Piperazine-2-carboxylic acid, 2,5 dichloro benzoic acid, 2, dichloro benzoic acid, 3-methyl benzoic acid, and allyl alkanoic acids.

In yet another embodiment of the present invention, the compound 21 used in step (b) of a process for preparation of cyclic aza-sila compounds of Formula I, is prepared by reacting (2E,4E)-hexa-2,4-dienoic acid with compound 3.

In still another embodiment of the present invention, a process for the preparation of 4,4 Dimethyl-1,4-azasilinan-1-yl)(phenyl) methanone (compound 4) comprises oxidizing 1-benzyl-4,4-dimethyl-1,4-azasilinane (compound of Formula 2) in presence of potassium permanganate to obtain 4,4 Dimethyl-1,4-azasilinan-1-yl)(phenyl) methanone.

DETAILED DESCRIPTION OF THE INVENTION

The present invention provides novel cyclic aza-sila compounds of Formula I. By the introduction of Silicon atom, these compounds expected to exhibit altered physico-chemical properties, in particular the lipophilicity of their molecules, which in turn may improve their properties for use as insect repellents.

According to a preferred embodiment of the present invention, the novel cyclic aza-sila compounds comprise the compound of Formula I:

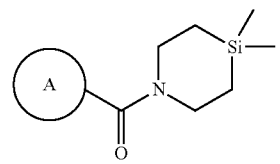

Formula I wherein, 'A' is selected from the group consisting of branched or unbranched (C1-C12) alkyl, branched or unbranched (C1-C12) alkynyl; and substituted or unsubstituted 4 to 6 membered acyclic saturated or unsaturated compounds, wherein the substituents are selected from the group consisting of halogen, hydrogen, (C1-C6) alkyl, aryl, arylalkyl, and heterocyclic;

or 'A' is independently selected from the group consisting of the following moiety:

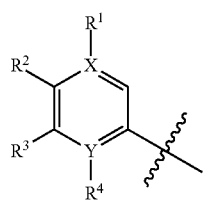

wherein, X and Y are identical or different and independently selected from the group consisting of C—, —N, —O, and —S;

where R1, R2, R3, and R4 are identical or different and are independently selected from the group consisting of hydrogen, halogen, linear or branched (C1-C6) alkyl, aryl, arylalkyl, hydroxyl, and heterocyclic; and wherein, the halogen is selected from the group consisting of —Cl, —I, —Br, and —F.

The key intermediate 4,4 dimethyl 1,4 azasilinane hydrochloride (3) in the preparation of compound of Formula I was prepared according to the procedure known in the literature (WO 2013/054275 A1) as shown in scheme 1 below.

Scheme 1

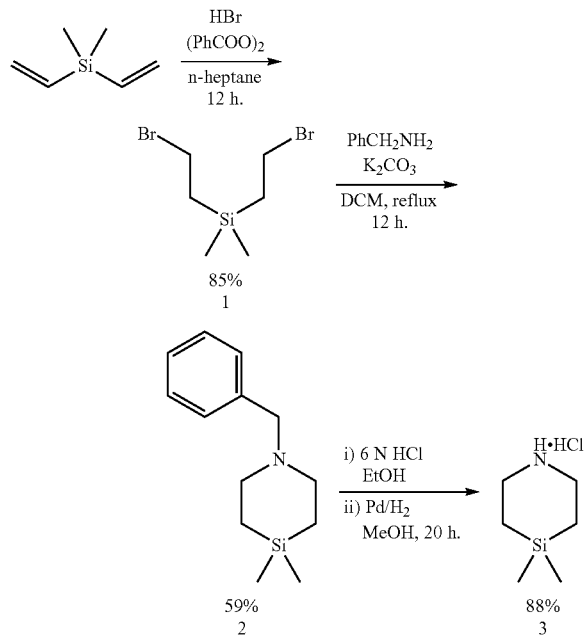

The compound 2 (1-benzyl-4,4-dimethyl-1,4-azasilinane) on oxidation in presence of potassium permanganate gave the cyclic aza-sila compound (4,4 Dimethyl-1,4-azasilinan-1-yl)(phenyl) methanone (compound 4) as per scheme 2.

Scheme 2

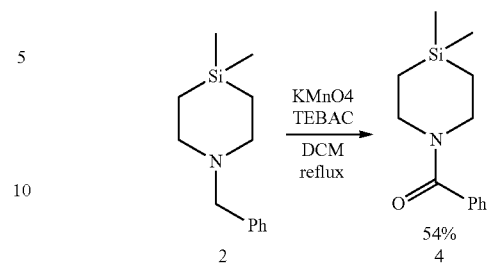

In yet another preferred embodiment, the invention provides alternate method of synthesizing compound of Formula I as per the scheme shown in scheme 3.

Scheme 3

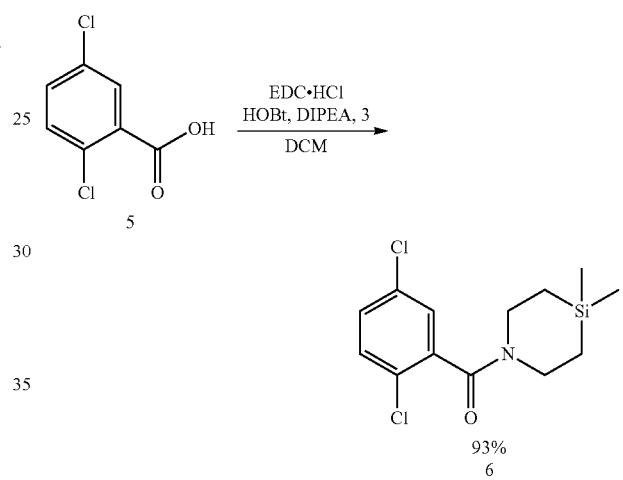

According to this method, substituted carboxylic acids are reacted with the silicon amine, 4,4-dimethyl-1,4-azasilinane hydrochloride (compound 3) by conventional acid amine coupling procedures using EDC.HCl (1-Ethyl-3-(3-dimethylaminopropyl)carbodiimide hydrochloride) and HOBt (Hydroxybenzotriazole) as coupling reagents to obtain desired cyclic aza-sila compounds of Formula I. One preferred cyclic aza-sila compounds prepared according to the invention is (2,5-dichlorophenyl)(4,4-dimethyl-1,4-azasilinan-1-yl)methanone(6), as shown in scheme 3.

Similarly, the invention provides compounds of Formula I prepared according to scheme 3 by varying the carboxylic acids, a series of sila analogs have been prepared as summarized in the below table 1.

TABLE 1

| Compound Code | Structure | Yield |
|---|---|---|
| 7 | 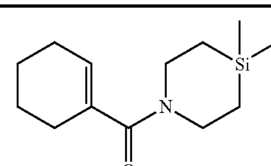 | 67% |

TABLE 1-continued
| Compound Code | Structure | Yield |
|---|---|---|
| 8 | 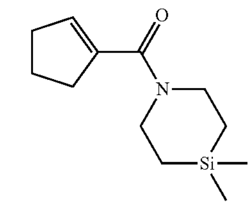 | 73% |
| 9 | 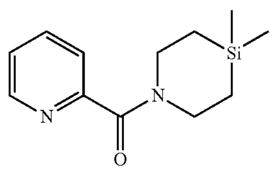 [SMILES: C[Si]1(C)CCN(C(=O)c2ccccn2)CC1] | 56% |
| 10 | 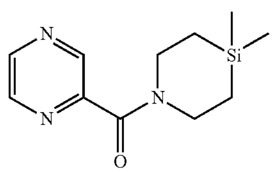 [SMILES: C[Si]1(C)CCN(C(=O)c2cnccn2)CC1] | 63% |
| 11 | 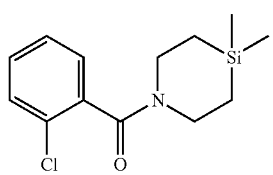 [SMILES: C[Si]1(C)CCN(C(=O)c2ccccc2Cl)CC1] | 72% |
| 12 | 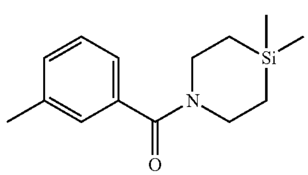 | 56% |
| 13 | 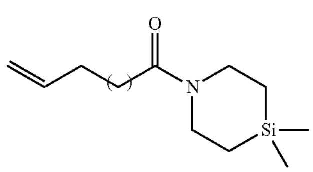 | 63% |
| 14 | 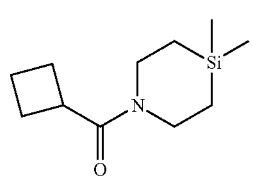 | 32% |
| 15 | 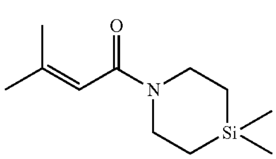 | 90% |
TABLE 1-continued
| Compound Code | Structure | Yield |
|---|---|---|
| 16 | | 64% |
| 17 | | 62% |
| 18 | | 57% |
The unsaturation present in the sila analogs of compound of Formula I reported in table 1 may optionally be hydrogenated using Pd on carbon to obtain saturated analogs of the corresponding compound of Formula I as shown in schemes 4 to 8.
SCHEME 4
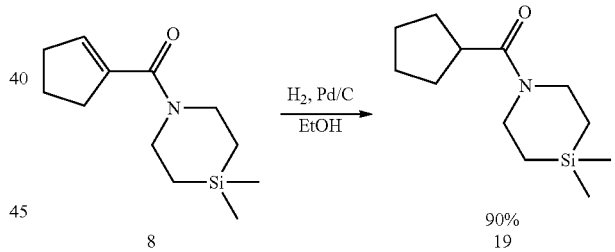
SCHEME 5
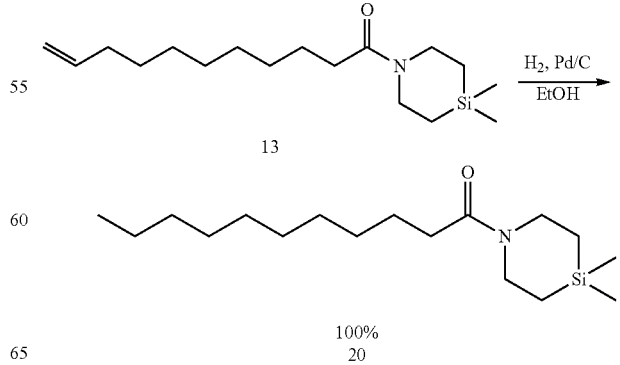

9

SCHEME 6

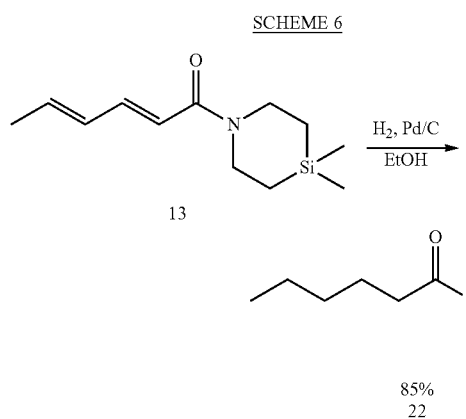

SCHEME 7

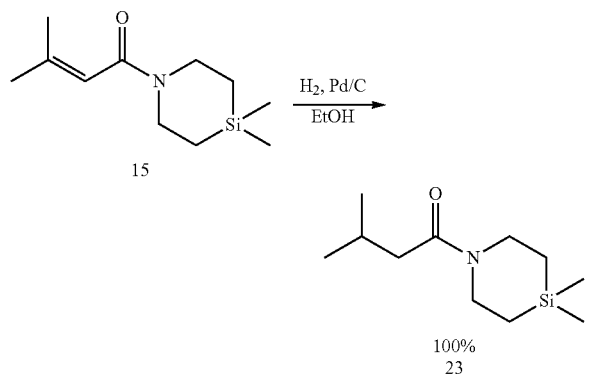

SCHEME 8

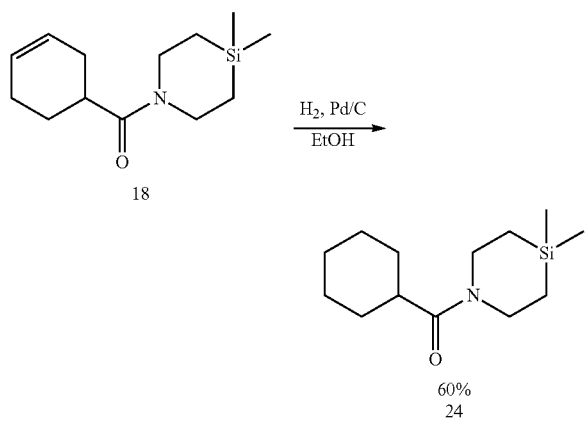

In yet another embodiment, the compounds of Formula I prepared according to the present invention are tested for their insect repellent activity.

The invention will now be illustrated with help of examples. The aforementioned embodiments and below mentioned examples are for illustrative purpose and are not meant to limit the scope of the invention. Various modifications of aforementioned embodiments and below mentioned examples are readily apparent to a person skilled in the art. All such modifications may be construed to fall within the scope and limit of this invention as defined by the appended claims.

EXAMPLES

Following examples are given by way of illustrating the present invention and should not be construed to limit the scope of the invention.

The intermediate compounds compound 2(1-benzyl-4,4-dimethyl-1,4-azasilinane) and compound 3(4,4 dimethyl 1,4 azasilinane hydrochloride) in the preparation of compound of Formula I were prepared according to procedure known in the literature (WO 2013/054275 A1) as shown in scheme 1.

Example 1: Synthesis of (4,4-Dimethyl-1,4-azasilinan-1-yl)(phenyl)methanone (compound 4)

To a solution of compound 2(1-benzyl-4,4-dimethyl-1,4-azasilinane) (150 mg, 0.7 mmol) in DCM was added Benzyltriethylammoniumchloride (467 mg, 2.1 mmol) and $KMnO_4$ (324 mg, 2.1 mmol). The reaction mixture was refluxed for 3 h, quenched with aq. Sodium thiosulphate, organic layer was separated, dried over $Na_2SO_4$ and concentrated under vacuum. The product was purified by column chromatography using pet ether-ethyl acetate mixtures (9:1) to afford compound 4 as a colourless solid (80 mg) in 54% yield. Melting Point: 65-67° C.; IR $v_{max}$(film): $cm^{-1}$ 3019, 1615, 1578, 1215; $^1$H NMR (400 MHz, $CDCl_3$): δ 7.36 (s, 5H), 3.85 (bs, 2H), 3.48 (bs, 2H), 0.91 (bs, 2H), 0.65 (bs, 2H), 0.11 (s, 6H); $^{13}$C NMR (100 MHz, $CDCl_3$): δ 170.7, 136.9, 129.0, 128.2 (2C), 126.2 (2C), 46.8, 41.9, 15.0, 13.6, −3.2 (2C).

Example 2: Synthesis of (2,5-Dichlorophenyl)(4,4-dimethyl-1,4-azasilinan-1-yl)methanone (compound 6)

To a solution of commercially available 2,5-dichlorobenzoic acid in dry DCM, was added EDC.HCl (168 mg, 1.1 mmol), HOBt (146 mg, 1.1 mmol) and diisopropylethyl amine (0.4 mL, 2.3 mmol) at 0° C. Then the silicon amine salt 3 (150 mg, 0.9 mmol) was added and stirred at RT for 8-10 h. To the reaction mixture water was added and the organic layer was separated, washed with saturated $NaHCO_3$, 1N HCl, dried over $Na_2SO_4$ and concentrated under reduced pressure. This crude mixture was purified by column chromatography using pet ether-ethyl acetate (95:5) to give the title compound 6 (255 mg) as a white solid in 93% yield. Melting Point: 79-81° C.; IR $v_{max}$(film): $cm^{-1}$ 3062, 2952, 1651, 1588; $^1$HNMR (400 MHz, $CDCl_3$): δ 7.34 (m, 1H), 7.30-7.27 (m, 2H), 4.02 (m, 1H), 3.77 (m, 1H), 3.40 (m, 2H), 0.94 (m, 2H), 0.77 (m, 1H), 0.64 (m, 1H), 0.14 (m, 6H); $^{13}$C NMR (100 MHz, $CDCl_3$): δ 165.6, 137.9, 133.0, 130.9, 129.9, 128.6, 127.3, 46.5, 41.6, 14.8, 13.6, −3.0, −3.4.

Example 3: Synthesis of Compounds 7-18

A series of analogues (compounds 3-15) were prepared by using the procedure described for the above compound 2, by varying the carboxylic acid.

Cyclohex-1-en-1-yl(4,4-dimethyl-1,4-azasilinan-1-yl)methanone (compound 7)

Yield—67%; IR $v_{max}$(film): $cm^{-1}$ 3068, 2938, 1688, 1644, 1283, 1260; $^1$H NMR (400 MHz, $CDCl_3$): δ 5.78 (m, 1H), 3.67 (bs, 4H), 2.21 (m, 2H), 2.01 (m, 2H), 1.70-1.61 (m, 4H), 0.78 (bs, 4H), 0.11 (s, 6H); $^{13}$C NMR (100 MHz, CDCl$_3$): δ 172.0, 134.7, 125.4, 46.0, 41.0, 25.9, 24.2, 21.8, 21.3, 15.2, 13.4, −3.3 (2C).

Cyclopent-1-en-1-yl(4,4-dimethyl-1,4-azasilinan-1-yl)methanone (compound 8)

Yield—73%; IR $ν_{max}$(film): cm$^{-1}$ 3050, 2952, 1714, 1615, 1251; $^1$H NMR (400 MHz, CDCl$_3$): δ 5.85 (m, 1H), 3.66 (m, 4H), 2.60 (m, 2H), 2.44 (m, 2H), 1.92 (qui, J=7.5 Hz, 2H), 0.77 (m, 4H), 0.10 (s, 6H); $^{13}$C NMR (100 MHz, CDCl$_3$): δ 169.0, 139.90, 130.50, 46.1, 41.4, 34.7, 33.2, 22.8, 15.6, 13.8, −3.1 (2C).

(4,4-Dimethyl-1,4-azasilinan-1-yl)(pyridin-2-yl)methanone (compound 9)

Yield—56%; Melting Point: 101-103° C.; IR $ν_{max}$(film): cm$^{-1}$ 3020, 1623, 1568, 1251; $^1$H NMR (400 MHz, CDCl$_3$): δ 8.58 (d, J=5.5 Hz, 1H), 7.77 (m, 1H), 7.55 (d, J=8.1 Hz, 1H), 7.32 (m, 1H), 3.90 (t, J=6.8 Hz, 2H), 3.58 (t, J=6.8 Hz, 2H), 0.96 (t, J=6.6 Hz, 2H), 0.81 (t, J=6.7 Hz, 2H), 0.13 (s, 6H); $^{13}$C NMR (100 MHz, CDCl$_3$): δ 168.1, 155.1, 148.4, 136.8, 124.0, 122.7, 46.6, 42.3, 15.0, 13.6, −3.1 (2C).

(4,4-Dimethyl-1,4-azasilinan-1-yl)(pyrazin-2-yl)methanone (compound 10)

Yield—63%; IR $ν_{max}$(film): cm$^{-1}$ 2988, 1638, 1572, 1483, 1267; $^1$HNMR (400 MHz, CDCl$_3$): δ 8.86 (m, 1H), 8.62 (m, 1H), 8.55 (m, 1H), 3.91 (t, J=6.6 Hz, 2H), 3.60 (t, J=6.6 Hz, 2H), 0.97, (t, J=7.2 Hz, 2H), 0.86 (t, J=7.2 Hz, 2H), 0.15 (s, 6H); $^{13}$C NMR (100 MHz, CDCl$_3$): δ 165.6, 150.4, 144.9, 144.6, 142.7, 46.8, 42.6, 15.1, 13.7, −3.1 (2C).

(2-Chlorophenyl)(4,4-dimethyl-1,4-azasilinan-1-yl)methanone (compound 11)

Yield—72%; IR $ν_{max}$(film): cm$^{-1}$ 3060, 2891, 1651, 1594; $^1$HNMR (400 MHz, CDCl$_3$): δ 7.40 (m, 1H), 7.32-7.28 (m, 3H), 4.06 (m, 1H), 3.78 (m, 1H), 3.40 (m, 2H), 0.95 (m, 2H), 0.76 (m, 1H), 0.61 (m, 1H), 0.13 (m, 6H); $^{13}$C NMR (100 MHz, CDCl$_3$): δ 167.2, 136.6, 130.2, 129.8, 129.7, 127.3, 127.0, 46.5, 41.6, 14.8, 13.7, −2.9, −3.3.

(4,4-Dimethyl-1,4-azasilinan-1-yl)(m-tolyl)methanone (compound 12)

Yield—56%; Melting Point: 65-68° C.; IR $ν_{max}$(film): cm$^{-1}$ 3018, 1618, 1585, 1252; $^1$HNMR (400 MHz, CDCl$_3$): δ 7.27 (m, 1H), 7.21-7.17 (m, 3H), 3.87 (m, 2H), 3.51 (m, 2H), 2.37 (s, 3H), 0.93 (m, 2H), 0.69 (m, 2H), 0.13 (s, 6H); $^{13}$C NMR (100 MHz, CDCl$_3$): δ 171.0, 138.2, 136.9, 129.8, 128.2, 126.9, 123.2, 47.0, 41.9, 21.4, 15.1, 13.7, −3.1 (2C).

1-(4,4-Dimethyl-1,4-azasilinan-1-yl)undec-10-en-1-one (compound 13)

Yield—63%; IR $ν_{max}$(film): cm$^{-1}$ 3077, 2929, 1651, 1456, 1251; $^1$HNMR (400 MHz, CDCl$_3$): δ 5.75 (m, 1H), 4.96-4.87 (m, 2H), 3.65 (t, J=6.3 Hz, 2H), 3.54 (t, J=6.0 Hz, 2H), 2.28 (t, J=7.3 Hz, 2H), 2.00 (m, 2H), 1.59 (m, 2H), 1.34-1.21 (m, 10H), 0.73 (m, 4H), 0.06 (s, 6H); $^{13}$C NMR (100 MHz, CDCl$_3$): δ 171.7, 139.0, 114.0, 45.1, 41.9, 33.7, 33.1, 29.4, 29.3, 29.2, 29.0, 28.8, 25.4, 15.0, 13.5, −3.2 (2C).

Cyclobutyl(4,4-dimethyl-1,4-azasilinan-1-yl)methanone (compound 14)

Yield—32%; IR $ν_{max}$(film): cm$^{-1}$ 2950, 1640, 1251; $^1$HNMR (400 MHz, CDCl$_3$): δ 3.69 (t, J=6.4 Hz, 2H), 3.48 (t, J=6.7 Hz, 2H), 3.27 (qui, J=8.4 Hz, 1H), 2.36 (m, 2H), 2.12 (m, 2H), 1.91 (m, 2H), 0.78 (t, J=6.3 Hz, 2H), 0.72 (m, 2H), 0.09 (s, 6H); $^{13}$C NMR (100 MHz, CDCl$_3$): δ 173.2, 44.4, 42.0, 37.3, 25.4 (2C), 17.9, 15.2, 13.6, −3.1 (2C).

1-(4,4-Dimethyl-1,4-azasilinan-1-yl)-3-methylbut-2-en-1-one (compound 15)

Yield—90%; IR $ν_{max}$(film): cm$^{-1}$ 3017, 1656, 1606, 1252; $^1$HNMR (400 MHz, CDCl$_3$): δ 5.82 (s, 1H), 3.73 (t, J=6.3 Hz, 2H), 3.61 (t, J=6.5 Hz, 2H), 1.90 (s, 3H), 1.83 (s, 3H), 0.82 (t, J=6.3 Hz, 2H), 0.74 (t, J=6.3 Hz, 2H), 0.10 (s, 6H); $^{13}$C NMR (100 MHz, CDCl$_3$): δ 167.3, 144.9, 118.4, 45.7, 41.4, 26.0, 20.0, 15.0, 13.7, −3.1 (2C).

(4,4-Dimethyl-1,4-azasilinan-1-yl)(o-tolyl)methanone (compound 16)

Yield—64%; IR $ν_{max}$(film): cm$^{-1}$ 3063, 2924, 1631, 1251; $^1$HNMR (400 MHz, CDCl$_3$): δ 7.27-7.16 (m, 4H), 4.16 (m, 1H), 3.64 (m, 1H), 3.39 (m, 2H), 2.30 (s, 3H), 0.94 (m, 2H), 0.62 (m, 2H), 0.12 (s, 6H); $^{13}$C NMR (100 MHz, CDCl$_3$): δ 170.3, 136.9, 133.8, 130.2, 128.5, 125.7, 125.4, 46.3, 41.3, 18.9, 14.9, 13.8, −2.8, −3.4.

(4,4-Dimethyl-1,4-azasilinan-1-yl)(p-tolyl)methanone (compound 17)

Yield—62%; IR $ν_{max}$(film): cm$^{-1}$ 2957, 1630, 1252; $^1$HNMR (400 MHz, CDCl$_3$): δ 7.30 (d, J=7.5 Hz, 2H), 7.19 (d, J=7.5 Hz, 2H), 3.86 (m, 2H), 3.53 (m, 2H), 2.37 (s, 3H), 0.93 (m, 2H), 0.68 (m, 2H), 0.13 (s, 6H); $^{13}$C NMR (100 MHz, CDCl$_3$): δ 171.0, 139.1, 134.0, 128.9 (2C), 126.4 (2C), 47.0, 42.0, 21.3, 15.1, 13.6, −3.1 (2C).

Cyclohex-3-en-1-yl(4,4-dimethyl-1,4-azasilinan-1-yl)methanone (compound 18)

Yield—57%; IR $ν_{max}$(film): cm$^{-1}$ 3024, 2922, 1727, 1637, 1250; $^1$H NMR (200 MHz, CDCl$_3$): δ 5.71 (m, 2H), 3.67 (m, 4H), 2.69 (m, 1H), 2.35 (m, 1H), 2.14-2.02 (m, 3H), 1.84-1.72 (m, 2H), 0.81 (m, 4H), 0.11 (s, 6H); $^{13}$C NMR (50 MHz, CDCl$_3$): δ 174.7, 126.3, 125.8, 44.9, 42.2, 36.3, 28.4, 25.9, 24.8, 15.6, 13.6, −3.1, −3.2.

Example 4: Synthesis of Cyclopentyl(4,4-dimethyl-1,4-azasilinan-1-yl)methanone (compound 19)

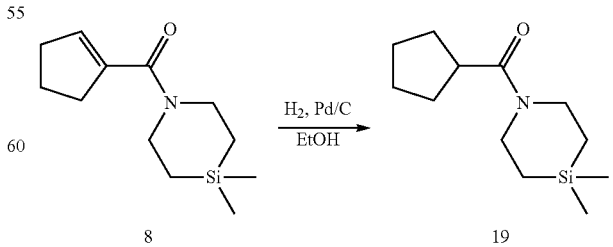

To a solution of 8 (cyclopent-1-en-1-yl(4,4-dimethyl-1,4-azasilinan-1-yl)methanone) (200 mg, 0.9 mmol) in Ethanol was added 10% Pd/C (10 mg) and stirred at RT for 1 h under Hydrogen atmosphere. The reaction mixture was filtered through celite pad and the filtrate was concentrated under reduced pressure to give compound 19 as a pale yellow liquid (180 mg) with a yield of 90%. IR $\nu_{max}$(film): cm$^{-1}$ 2953, 1654, 1252; $^1$HNMR (400 MHz, CDCl$_3$): δ 3.65 (t, J=6.5, 2H), 3.60 (t, J=6.2 Hz, 2H), 2.84 (qui, J=8.2 Hz, 1H), 1.79-1.68 (m, 6H), 1.53-1.49 (m, 2H), 0.72 (m, 4H), 0.05 (s, 6H); $^{13}$C NMR (100 MHz, CDCl$_3$): δ 174.7, 44.8, 42.1, 40.9, 30.4 (2C), 26.0 (2C), 15.3, 13.6, −3.1 (2C).

Example 5: Synthesis of Compounds 20-24

The procedure for hydrogenation described in example 4 was followed for the preparation of compounds 20, 22, 23 and 24.

1-(4,4-Dimethyl-1,4-azasilinan-1-yl)undecan-1-one (compound 20)

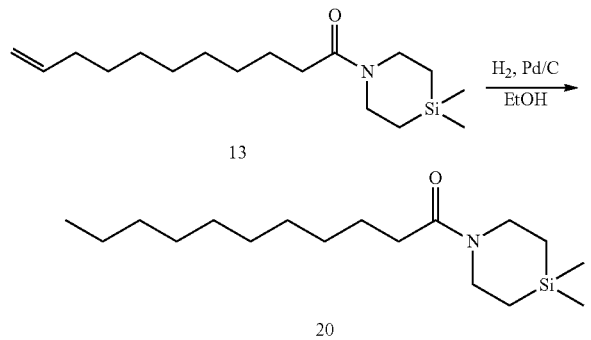

Yield—100%; IR $\nu_{max}$ (film): cm$^{-1}$ 2925, 1639, 1251; $^1$HNMR (400 MHz, CDCl$_3$): δ 3.70 (t, J=7.5 Hz, 2H), 3.58 (t, J=7.5 Hz, 2H), 2.32 (t, J=8.2 Hz, 2H), 1.64 (m, 2H), 1.31-1.26 (m, 14H), 0.88 (m, 2H), 0.78 (m, 4H), 0.10 (s, 6H); $^{13}$CNMR (100 MHz, CDCl$_3$): δ 171.9, 45.1, 42.0, 33.2, 31.8, 29.5 (3C), 29.4, 29.3, 25.5, 22.6, 15.1, 14.0, 13.6, −3.1 (2C).

1-(4,4-Dimethyl-1,4-azasilinan-1-yl)hexan-1-one (compound 22)

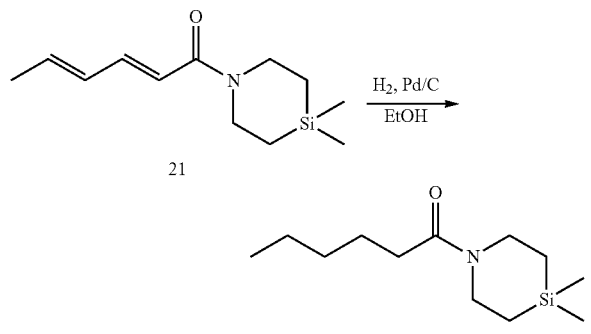

The starting material 21 was prepared from (2E,4E)-hexa-2,4-dienoic acid and compound 3 following the procedure in Scheme 3 with a yield of 93%. It was then subjected to hydrogenation to give the compound 22. Yield—85%; IR $\nu_{max}$(film): cm$^{-1}$ 2956, 1652, 1251; $^1$HNMR (400 MHz, CDCl$_3$): δ 3.70 (t, J=6.6 Hz, 2H), 3.58 (t, J=6.3 Hz, 2H), 2.32 (t, J=7.5 Hz, 2H), 1.68-1.57 (m, 4H), 1.36-1.29 (m, 3H), 0.94-0.73 (m, 6H), 0.10 (s, 6H); $^{13}$C NMR (100 MHz, CDCl$_3$): δ 171.9, 45.2, 42.0, 33.2, 31.7, 25.2, 22.5, 15.2, 14.0, 13.6, −3.0 (2C).

1-(4,4-Dimethyl-1,4-azasilinan-1-yl)-3-methylbutan-1-one (compound 23)

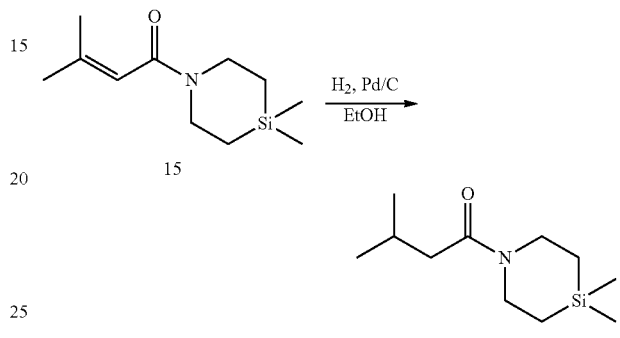

Yield—100%; IR $\nu_{max}$(film): cm$^{-1}$ 2957, 1638, 1252; $^1$HNMR (400 MHz, CDCl$_3$): δ 3.66 (t, J=6.3 Hz, 2H), 3.55 (t, J=6.0 Hz, 2H), 2.18-2.07 (m, 3H), 0.92 (d, J=6.3 Hz, 6H), 0.73 (m, 4H), 0.06 (s, 6H); $^{13}$C NMR (100 MHz, CDCl$_3$): δ 171.0, 45.2, 41.9, 41.8, 25.6, 22.7, 15.0, 13.6, −3.2 (2C).

Cyclohexyl(4,4-dimethyl-1,4-azasilinan-1-yl)methanone (compound 24)

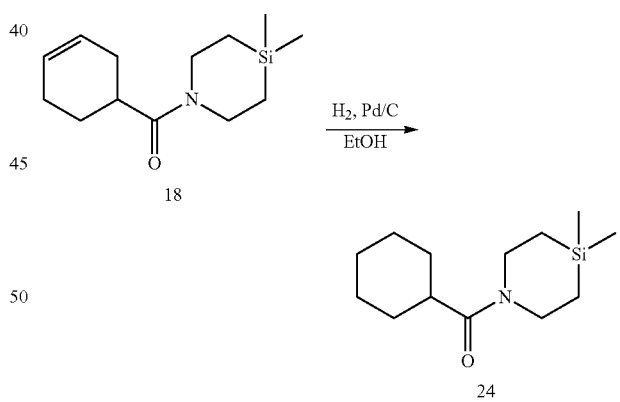

Yield—60%; IR $\nu_{max}$(film): cm$^{-1}$ 3020, 2932, 1617, 1253; $^1$H NMR (400 MHz, CDCl$_3$): δ 3.67 (d, J=6.4 Hz, 2H), 3.59 (d, J=6.4 Hz, 2H), 2.45 (m, 1H), 1.79-1.47 (m, 7H), 1.31-1.20 (m, 3H), 0.76 (m, 4H), 0.08 (s, 6H); $^{13}$C NMR (100 MHz, CDCl$_3$): δ 175.0, 44.9, 42.1, 40.5, 29.7 (2C), 25.9 (2C), 25.8, 15.6, 13.7, −3.1 (2C).

Example 6: Determination of Insect Repellant Activity

Mosquito repellence activity was assessed on the basis of protection period (hr) offered by various analogues of DEET against Mosquito bites. The protection period was measured on the basis of the concept" time until the first bite" pioneered by Granette (Comparison of mosquito repellence test under laboratory and field conditions. Granett, P. *Proc Ann Meet NJ Mosq Assoc,* 1938, vol. 25, 51). Repellence tests were carried out against 3-5 days old, blood starved but sucrose fed (0.5M solution), *Ae. aegypti* females mosquitoes, drawn from well-established laboratory colony maintained at 27±1° C. Temperature and 70±5% Relative humidity. The light intensity was regulated at 300-500 lux for testing against laboratory, colonized *Ae. aegypti*, a day biting mosquito. Human volunteer's hand covered with polythene disposable gloves was introduced in the cage containing about 200 hungry mosquitoes. Mosquitoes were allowed to bite on the back of the hand through muslin screen stuck over a small window (2 cm×2 cm) cut out in the polythene bag. Various analogues of DEET were loaded on the muslin cloth screen instead of direct skin application so as to avoid the potential risk involved in the evaluation of natural products of unknown mammalian toxicity. All the test solutions were made in Analar grade Acetone The muslin cloth screen was first treated with the analogue taking two doses @0.25 mg/cm2 and 0.5 mg/cm2 and the solvent was evaporated before use. Control muslin screen was treated with solvent alone. After introduction of the hand covered with the polythene glove with the treated muslin screen into the mosquito cage, number of mosquito bites received in subsequent 5 minutes was counted. In the event of no bites in the initial 5 minutes exposure, the test hand was exposed repeatedly after every consecutive ½ hr for 5 minutes test till the time a confirmed bite was received. Number of hours before the receipt of a confirmed bite (Techniques for the evaluation of insect repellents. A critical review (Schreck, C. E, *Ann Rev Entomol,* 1977, vol 22, 101) represented the protection period offered by the test compound. In control rate of mosquito bite was 10-12 bites/min. All the tests were carried out at 27±1° C. temperature between 9.00-17.00 hrs.

| Compound | Protection period in hrs @ 0.25 mg/cm$^2$ | Protection period in hrs @ 0.50 mg/cm$^2$ |
|---|---|---|
| 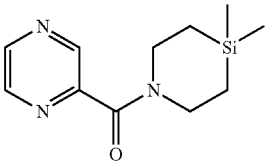<br>10 | 2.14 ± 0.76 | 4.22 ± 0.69 |
| 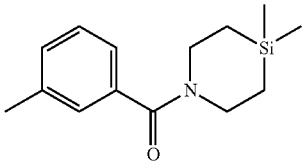<br>12 | 1.47 ± 0.13 | 2.15 ± 0.072 |
| 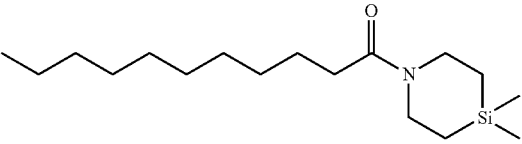<br>20 | 2.14 ± 0.065 | 5.05 ± 0.207 |
| 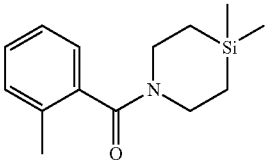 [SMILES: Cc1ccccc1C(=O)N1CC[Si](C)(C)CC1]<br>16 | 4.09 ± 0.053 | 5.41 ± 0.135 |
| 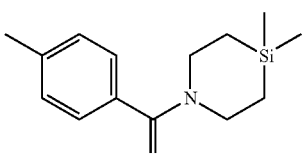<br>17 | 3.08 ± 0.056 | 4.16 ± 0.067 |

ADVANTAGES OF THE INVENTION

1. Cyclic aza-sila compounds of Formula I are useful as insect repellents.
2. Claimed compounds may not cause any adverse health issues in animal.

LIST OF ABBREVIATIONS

DEET (N,N-Diethyl-meta-toluamide)
DEPA (N, N-Diethyl phenylacetamide)
DCM (Dichloromethane)
TEBAC (Benzyltriethylammonium chloride)
EDC.HCl (Ethylcarbodiimide hydrochloride)
HOBt (Hydroxybenzotriazole)
DIPEA (N,N-Diisopropylethylamine)
RT (room temeperature)

We claim:
1. A cyclic aza-sila compound of Formula I,

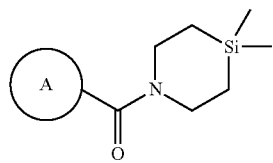

Formula I wherein, 'A' is selected from the group consisting of unbranched (C4-C12) alkyl, branched or unbranched (C1-C12) alkynyl, and substituted or unsubstituted 4 to 6 membered acyclic or cyclic saturated or unsaturated compounds;
wherein the substituents are selected from the group consisting of halogen, hydrogen, (C1-C6) alkyl, aryl, and heterocyclic;
or 'A' is independently selected from the group consisting of the following moiety:

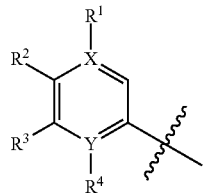

wherein, X and Y are identical or different and independently selected from the group consisting of —C—, —N, —O, and —S;
where R1, R2, R3, and R4 are identical or different and are independently selected from the group consisting of hydrogen, halogen, linear or branched (C1-C6) alkyl, aryl, arylalkyl, hydroxyl, and heterocyclic; and
wherein, the halogen is selected from the group consisting of —Cl, —I, —Br, and —F.

2. The cyclic aza-sila compound as claimed in claim 1, wherein the representative compounds of Formula I are selected from the group consisting of:
(4,4-Dimethyl-1,4-azasilinan-1-yl)(phenyl)methanone [compound 4];
(2,5-dichlorophenyl)(4,4-dimethyl-1,4-azasilinan-1-yl) methanone [compound 6];
Cyclohex-1-en-1-yl(4,4-dimethyl-1,4-azasilinan-1-yl) methanone [compound 7];
Cyclopent-1-en-1-yl(4,4-dimethyl-1,4-azasilinan-1-yl) methanone [compound 8];
(4,4-Dimethyl-1,4-azasilinan-1-yl)(pyridin-2-yl)methanone [compound 9];
(4,4-Dimethyl-1,4-azasilinan-1-yl)(pyrazin-2-yl)methanone [compound 10];
(2-Chlorophenyl)(4,4-dimethyl-1,4-azasilinan-1-yl) methanone [compound 11];
(4,4-Dimethyl-1,4-azasilinan-1-yl)(m-tolyl)methanone [compound 12];
1-(4,4-Dimethyl-1,4-azasilinan-1-yl)undec-10-en-1-one [compound 13];
Cyclobutyl(4,4-dimethyl-1,4-azasilinan-1-yl)methanone [compound 14];
1-(4,4-Dimethyl-1,4-azasilinan-1-yl)-3-methylbut-2-en-1-one [compound 15];
(4,4-Dimethyl-1,4-azasilinan-1-yl)(o-tolyl)methanone [compound 16];
(4,4-Dimethyl-1,4-azasilinan-1-yl)(p-tolyl)methanone [compound 17];
Cyclohex-3-en-1-yl(4,4-dimethyl-1,4-azasilinan-1-yl) methanone [compound 18];
Cyclopentyl-(4,4-dimethyl-1,4-azasilinan-1-yl)methanone [compound 19];
1-(4,4-Dimethyl-1,4-azasilinan-1-yl)undecan-1-one [compound 20];
1-(4,4-Dimethyl-1,4-azasilinan-1-yl)hexan-1-one [compound 22];
1-(4,4-Dimethyl-1,4-azasilinan-1-yl)-3-methylbutan-1-one [compound 23]; and
Cyclohexyl(4,4-dimethyl-1,4-azasilinan-1-yl)methanone [compound 24].

3. The cyclic aza-sila compound as claimed in claim 1 for use as an insect repellent.

4. A process for the preparation of cyclic aza-sila compounds of Formula I, said process comprising the steps of:
(a) acid-amine coupling of 2 (1-benzyl-4,4-dimethyl-1,4-azasilinane) of Formula 3 with a substituted carboxylic acid in presence of EDC.HCl(1-Ethyl-3-(3-dimethyl-aminopropyl)carbodiimide hydrochloride) and HOBt (Hydroxybenzotriazole) as coupling reagents in an organic base to obtain compounds selected from the group consisting of compound 6, compound 7, compound 8, compound 9, compound 10, compound 11, compound 12, compound 13, compound 14, compound 15, compound 16, compound 17, and compound 18;
(b) optionally hydrogenating a compound selected from the group consisting of compound 8, 13, 15, and 18, as obtained in step (a) or compound 21 in ethanol by adding 10% Pd on carbon followed by stirring at room temperature for 1 h under Hydrogen atmosphere to obtain a compound selected from the group consisting of compound 19, 20, 23, 24, and 22 respectively.

5. The process as claimed in claim 4, wherein the substituted carboxylic acid is selected from the group consisting of cyclohexene carboxylic acid, cyclopentene carboxylic acid, pyridine carboxylic acid, Piperazine-2-carboxylic acid, 2, 5 dichloro benzoic acid, 2, dichloro benzoic acid, 3-methyl benzoic acid, and allyl alkanoic acids.

6. The process as claimed in claim 4, wherein compound 21 used in step (b) is prepared by reacting (2E,4E)-hexa-2, 4-dienoic acid with compound 3.

7. A process for the preparation of 4,4 Dimethyl-1,4-azasilinan-1-yl)(phenyl) methanone (compound 4), the process comprising:

oxidizing 1-benzyl-4,4-dimethyl-1,4-azasilinane of Formula 2 in the presence of potassium permanganate to obtain 4,4 Dimethyl-1,4-azasilinan-1-yl)(phenyl)methanone.

* * * * *